United States Patent [19]

Sheldon et al.

[11] Patent Number: 4,482,680

[45] Date of Patent: Nov. 13, 1984

[54] QUATERNARY AMMONIUM GROUP-CONTAINING POLYMERS HAVING ANTIMICROBIAL ACTIVITY

[75] Inventors: Bernard G. Sheldon, Palo Alto; Robert E. Wingard, Jr., Mountain View; Ned M. Weinshenker, Palo Alto; Daniel J. Dawson, Los Altos, all of Calif.

[73] Assignee: Dynapol, Palo Alto, Calif.

[21] Appl. No.: 484,721

[22] Filed: Apr. 13, 1983

Related U.S. Application Data

[63] Continuation of Ser. No. 302,684, Sep. 15, 1981, abandoned.

[51] Int. Cl.$^3$ .................... C08F 114/02; A01N 33/12; C08F 214/02
[52] U.S. Cl. .............................. 525/331.4; 525/333.3; 525/379; 525/380; 525/381; 525/326.7; 525/327.1; 525/328.2; 525/329.4; 521/27; 424/78; 424/329; 526/293
[58] Field of Search .................... 424/78, 329; 521/27; 525/330.1–330.9, 381, 331.4, 333.3, 379, 380; 526/293

[56] References Cited

U.S. PATENT DOCUMENTS

| | | | |
|---|---|---|---|
| 2,772,310 | 11/1956 | Morris | 564/288 |
| 3,898,088 | 8/1975 | Cohen et al. | 525/330 |
| 3,931,319 | 1/1976 | Green et al. | 424/244 |
| 3,944,424 | 3/1976 | Cohen et al. | 525/330 |
| 3,963,662 | 6/1976 | Fujiwara et al. | 521/27 |
| 4,087,599 | 5/1978 | Roe et al. | 525/330 |

*Primary Examiner*—Albert T. Meyers
*Assistant Examiner*—John M. Kilcoyne
*Attorney, Agent, or Firm*—Burns, Doane, Swecker & Mathis

[57] ABSTRACT

Polymeric quaternary ammonium compounds having recurring vinylbenzyl ammonium units are disclosed. The quaternary ammonium units preferably have 2 alkyl substituents of 1 to 4 carbons and 1 alkyl substituent of 4 to 12 carbons. These materials have antimicrobial properties and are particularly useful for preserving ophthalmic solutions.

9 Claims, No Drawings

QUATERNARY AMMONIUM GROUP-CONTAINING POLYMERS HAVING ANTIMICROBIAL ACTIVITY

This application is a continuation of application Ser. No. 302,684 filed Sept. 15, 1981, now abandoned.

BACKGROUND OF THE INVENTION

1. Field of the Invention

This invention relates to quaternary ammonium group-containing polymers. More particularly it concerns a family of such polymers that exhibit antimicrobial activity and their application as antimicrobials.

2. Prior Art

Quaternary ammonium group-containing polymers have been widely studied. A review of the literature has turned up a vast collection of references to the general subject. As this invention relates to quaternary ammonium polymeric compounds having antimicrobial activity as well as to certain new copolymeric quaternary polymers, three references to Green et al. may be of interest. These references, U.S. Pat. Nos. 3,931,319; 4,005,193; and 4,025,617, disclose polymeric quaternary ammonium polymers having antimicrobial activity. However, Green et al.'s polymers are structurally dissimilar to the present materials.

The polymers of the invention may be classified as having a poly(vinylbenzyl quaternary ammonium) halide structure. In certain embodiments, they have a copolymer structure with repeating

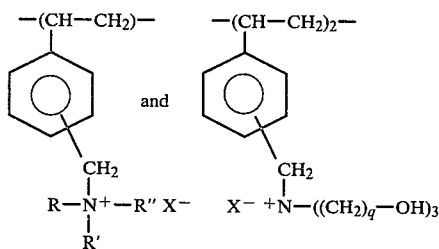

$X^-$ = physiologically acceptable anion
R's = alkyls
q = 1 to 4, preferably 2 units.

U.S. Pat. Nos. 2,702,795 of Gilwood; 2,772,310 of Morris; 3,563,949 of Hartenstein and 4,087,599 of Roe et al., as well as Journal of Polymer Science, Polymer Chemistry Edition, Vol. 18, pp. 455–65, 619–80, Dragan et al., are certainly of interest as they show similar groups but do not suggest the present materials.

These polymeric quaternary compounds fill a well indentified and recognized need for a polymeric antimicrobial agent similar to or surpassing known nonpolymeric species such as hexachlorophene, Zephiran ® and the like. Being large polymeric molecules, the present materials are less mobile and less likely to migrate or inappropriately penetrate or be absorbed into substrates. This permits their use in environments where penetration or displacement or volatilization are problems. Further, it permits residual antimicrobial activity to be imparted to surfaces and the like by the use of these materials.

STATEMENT OF THE INVENTION

It has now been discovered that polymeric quaternary amines having recurring vinylbenzyl ammonium groups of the structure

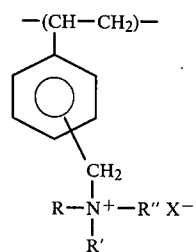

wherein R is a 4 to 12 carbon atom alkyl and R' and R" are each independently 1 to 4 carbon atom alkyls and $X^-$ is an anion such as halide, have antimicrobial activity. Such materials can be homopolymers but preferably are copolymers. These polymers and copolymers constitute aspects of this invention. Antimicrobial compositions based on them and their use constitute additional aspects.

DETAILED DESCRIPTION OF THE INVENTION

Definitions

The term "recurring" when used herein to describe mer units of a polymer is an inclusive term to describe homopolymers and copolymers with or without added copolymer units.

Molecular weights are expressed in daltons (D) and are determined by gel permeation chromatography comparison of experimental compounds with chemically similar standards of known molecular weight.

Weights, temperatures and pressures are given in metric units unless otherwise noted.

"Hygienically acceptable" refers to the property of being acceptable as a component of a material to be used to clean, disinfect or sterilize a human's or animal's physiological environment.

"Physiologically acceptable" means non-toxic and usable in materials contacting or consumed by mammals including man.

"Mer unit" means a discrete repeating unit within the polymer structure.

The Quaternary Ammonium Repeat Unit

The homopolymers and copolymers of this invention always contain a vinylbenzyl ammonium salt as a recurring mer unit. This unit has the structure

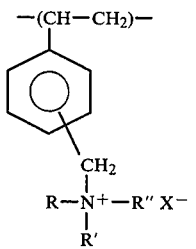

wherein R is a 4 to 12 carbon alkyl and R' and R" are the same or different 1 to 4 carbon atom alkyls. X is a physiologically acceptable anion. Preferably R is a 6 to 10 carbon atom linear or branched alkyl—i.e. hexyl, 2-ethylhexyl, octyl, decyl, nonyl, heptyl, 2,4-dimethylhexyl and the like. Also preferably R' and R" are 1 to 2 carbon atom alkyls—that is methyl or ethyl. Usually and more preferably, R' and R" are the same alkyl. The more preferred arrangement has R equal to an about 8 carbon atom alkyl. Most preferably R is n-octyl and R' and R" are each methyl.

Counterion $X^-$ may be any physiologically acceptable anion. However, usual preparative methods generally lead to a halide (e.g. $Cl^{31}$, $I^-$ or $Br^-$) with chloride ion being by far the most common.

Copolymeric Units

Optionally and preferably the polymers contain copolymeric units—herein the generic structure being depicted as —CU—. The units can be added for such down-to-earth purposes as to reduce the average cost per unit weight of the polymer or to "dilute" the active units and thus yield a more easily measured, handled or applied material. The copolymeric units can be added to achieve or enhance desired physical properties, as well. Such properties included greater antimicrobial activity, better solubility in aqueous or nonaqueous media, better miscibility in various media, enhanced dispersibility, enhanced film forming and the like.

The first type of "CU" units are represented by styrene and similar vinylaromatics and lower alkenes or alkadienes such as ethylene, butadiene and the like. The second type of CU units are illustrated by vinyl acetamide, vinyl amine, vinyl amine quaternized with hydroxyethylenes or similar water solubilizers or with hydrophobes such as dodecyls, or vinylbenzyl amine quaternized with three long chain alkyl hydrophobes or with three lower alkyl or hydroxyalkyl hydrophiles. Other units include for example vinyl acetate, vinyl alcohol, acrylic acid, acrylate and methacrylate esters; acrylamide and acrylamide derivatives including quaternized acrylamide; N-vinylimidazole and derivatives thereof including quaternized N-vinylimidazoles; 4-vinylpyridine and derivatives thereof including quaternized 4-vinylpyridines; N-vinylpyrrolidone and derivatives thereof; vinylbenzyl ethers of polyethylene glycols and their monoalkyl ethers. These units are all known in the art as are the methods for their incorporation into copolymers. Mixtures of two or more CU units may, of course, be used.

Generically, the CU's can be grouped as 2 to 6 carbon alkylenes or alkenylenes having pendent therefrom from 0 to 2 inclusive substitutent groups selected from aryls, alkaryls, and aralkyls of 6-8 carbons, alkyls of 1-4 carbons, amides, hydroxyls, carboxylic acids, and their esters, nitrogen-containing 5 or 6 atom heterocyclics and amine and ether-substituted aryls, alkaryls, and aralkyls.

One preferred group of copolymer units are vinylbenzyl amines quaternized by hydrophilic groups such as hydroxyalkyls of from 1 to 4 carbon atoms, particularly vinylbenzyl amines quaternized with three 2-hydroxyethylenes (i.e. with a triethanolamine structure). Such units are represented structurally as

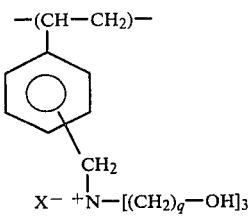

wherein q is 2 through 4 inclusive and most preferably 2.

Another preferred group of copolymer units are vinylbenzyl ethers of poly(ethylene glycol)s or their monoalkyl ethers, particularly methyl ethers. Such units are represented structurally as

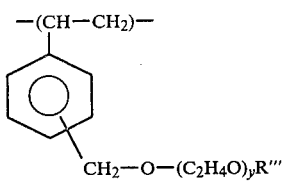

wherein y is 1 through 10 inclusive, preferably 1 through 4 inclusive, and R'" is a hydrogen or lower alkyl unit, such as from 1 to 4 carbons most generally methyl.

Molecular Size and Proportions of Units

The polymeric quaternary amines of this invention have at least about 10 mer units on average in each polymer molecule. Preferably they contain from 10 to about 2000 mer units. This gives rise to molecular weights for the homopolymer of from about 3000 to about 600,000 and for copolymers, of from about 1000 to a million or so, depending upon the unit and proportions employed. More preferably the number of mer units is from about 20 to about 1000.

The proportion of copolymeric mer units in the polymer can vary from 0 (homopolymer) to about 90% of the total. Among copolymers, those having at least about 20% of copolymer unit (CU's) are generally preferred. With less than this level, often the products have essentially the properties of the homopolymer.

This means that structurally the polymers can be represented as follows:

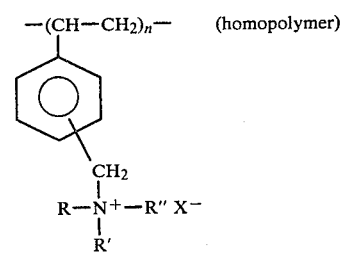

wherein R is a 4 to 12 carbon atom alkyl and R' and R" are 1 to 4 carbon alkyls and n is 10 to 2000 and X is an anion; and

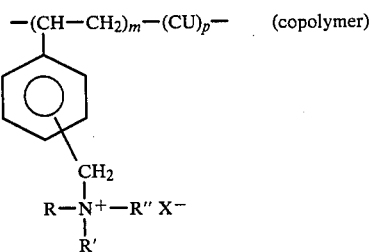

(copolymer)

wherein the R's and X and n are as set forth, m+p=n, p=0 to 0.9(n) preferably 0.2 to 0.9(n) and CU is a copolymeric unit.

The two preferred families of copolymers are represented by

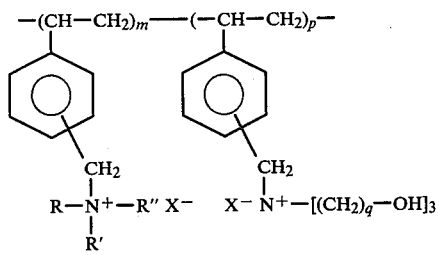

wherein m+p=n, q is 2 through 4 inclusive, and the R's and X$^-$ are as defined; and especially when R is octyl and R' and R" are each methyls, q is 2 and n is 20 to 100 and p is about 0.3 n; and

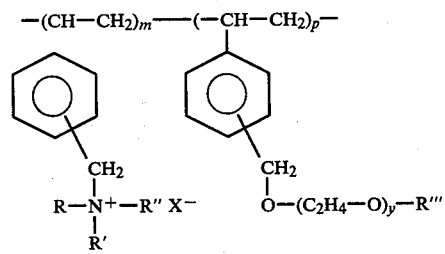

wherein m, p, X$^-$ and R, R', and R" are as defined and y is 1 to 10 preferably 1 through 4 inclusive and R''' is hydrogen or lower alkyl of 1 through 4 carbons, especially methyl.

Preparation of the Polymers

The polymers of this invention can be prepared by the general process of:

a. polymerizing vinylbenzyl halide plus any optional comonomer units using free-radical catalysis, and b. reacting the resulting poly(vinylbenzyl halide) with tertiary amine to yield the desired quaternary amine which is thereafter recovered.

In a representative preparation, the polymerization reaction is carried out with the monomer(s) in solution in an inert organic, often aromatic reaction medium such as toluene, benzene, tetrahydrofuran, or methylethyl ketone. It is of advantage to have an inert atmosphere, such as argon, over the reaction zone. A free-radical initiator such as a peroxide, or for example, AIBN (azobisisobutyronitrile) is employed in amounts of from 0.01 to 0.5% wt (basis monomer). The reaction is carried out at elevated temperatures, for example at temperatures of from 50° to 150° C., most commonly at the reflux temperature of the reaction medium. Elevated pressures may be employed to achieve temperatures above atmospheric reflux. The reaction takes a substantial period-often as long as several days. Of course, this period is related to the temperature employed with higher temperature requiring shorter time and lower temperature requiring longer times. As a guideline, at 75°-80° C. reaction temperature the reaction is complete in 18 to 24 hours. The polymeric intermediate product is recovered such as by precipitation following nonsolvent addition. The molecular weight of the resulting polymer can be varied by changing reaction conditions, such as the monomer and free radical initiator concentrations, solvent composition, and the reaction temperature as is known in the art.

The coupling of the tertiary amine to the poly(vinylbenzyl halide) is carried out in a relatively polar organic solvent system such as THF or alkanols or mixtures thereof. Examples of such solvent systems are tetrahydrofuran (THF), methanol, ethanol, isopropanol, isobutanol, THF:ethanol, THF:isopropanol, and THF:isobutanol. A preferred solvent system is 1:1 THF:isopropanol.

The reaction is carried out by admixing the poly(vinylbenzyl halide) and the tertiary amine in the reaction medium and heating. The amount of tertiary amine should be controlled. If a homopolymer product is desired—i.e. with all available benzyl halide groups reacted—it is of advantage to add an excess of amine, such as from about 1.0 to 1.5 or more equivalents of amine per mole of available benzyl halide. The excess is employed only to speed the reaction. In fact, the amine will react relatively quantitatively with available halide sites. Thus, when it is desired to react only a portion of the available halide sites with tertiary amine, less tertiary amine should be added. For example, when a 1:1 equivalent tertiary amine:trialkanol amine copolymer is desired, one generally adds about 0.5 equivalent of trialkyl amine, basis available sites.

This reaction is complete in 24 hours at 60°-80° C. The reactants are relatively heat stable so higher temperatures such as up to 150° C. can be employed without adversely affecting the reaction's yield. Thus temperatures from about 50° to 150° C. and times of 1 to 24 hours can be employed with temperatures of 60° to 140° C. being preferred.

Other reactants with the benzyl halide sites, for example trialkanolamines, can be added together with the trialkylamine or sequentially. If two materials are added at the same time, one must be careful not to add an excess of the more reactive material or else the reaction will not give the stoichiometry desired. Usually two materials are added sequentially. The coupling of the second material may be carried out in the same reaction medium without intermediate isolation of the product. The coupling of the second material generally employs similar reaction conditions to those used to couple the first.

After coupling, it is desirable to purify the final product to remove excess amines, salts and the like. Dialysis, ultrafiltration and other art-known processes for isolating and purifying polymers can be employed.

Formulation of Antimicrobial Compositions

The polymers of this invention are characterized as having antimicrobial activity. In this use they are formulated into antimicrobial compositions such as by being admixed with an hygienically acceptable carrier or vehicle.

This antimicrobial activity gives the materials utility as preservations for ophthalmic solutions, especially wetting solutions, cleaning solutions, cushioning solutions and soaking solutions for hard and soft contact lenses. In the case of soft contact lenses, the materials offer a special advantage of not absorbing and concentrating within the lens as monomeric antimicrobials and preservatives have been known to do. Other utilities are as preservations and/or antimicrobials for hair care, and topical pharmaceutical products. Other uses include incorporation in intra-vaginal anti-infectives, spermicides, therapeutic skin care (anti-acne) preparations and use as persistent deodorants or antimicrobials for body cavities such as the abdomen, lungs, or GI tract and the like. In addition, the products can be formulated with various cleanser components to form persistent disinfectants for home or hospital use.

In these applications, the products are generally admixed with a suitable carrier or medium such as sterile water or saline, gel salve bases, and the like in an antimicrobially effective amount—which amount is defined to be an amount sufficient to effect the desired antimicrobial or preserving action. Such amounts vary from as little as 10–20 ppm to as much as 1000 ppm (in finished product form) or up to 5% in concentrated formulations.

The amount employed will also vary somewhat depending upon the exact material employed. The most active materials appear to be those having a dimethyl-n-octyl ammonium salt configuration. Interestingly, as one increases or decreases the "long" group chain length say to $C_4$ or $C_{12}$ the activity falls off. At the "trimethyl" or "dimethyloctadecyl" extremes, antimicrobial activity is essentially absent. In general terms, this activity is as shown in Table 1.

TABLE I

| Compound | Antimicrobial Activity (relative units) |
|---|---|
| R = $C_2$ | 0.0 |
| $C_4$ | 0.1 |
| $C_6$ | 0.8 |
| $C_8$ | 1.0 |
| $C_{10}$ | 0.8 |
| $C_{12}$ | 0.2 |
| $C_{18}$ | 0.1 |

The antimicrobial formulations are prepared by conventional means of admixing, grinding and the like. In this regard, the polymers can be considered to be like other water-soluble salts and may be treated accordingly. No special formulation techniques are usually required.

The invention will be further described by the following examples. These are provided for purposes of illustration and are not to be considered as limiting the invention's scope.

EXAMPLE I

A. Preparation of Poly(chloromethylstyrene)

AIBN (3.8 g, 23.1 mmoles) and 100 ml of toluene were charged to a magnetically-stirred reactor flask. Then 152.5 g (1.00 mole) of chloromethylstyrene was added with toluene to give a 900 ml reaction volume. Argon gas was bubbled through the mixture and it was heated in an oil bath to 78°–80°. It was stirred for 22 hours at this temperature and then cooled.

The polymer was recovered by adding hexane and dropping the mixture into 1.5 l of hexane. A taffy-like precipitate formed, was collected, was rinsed in water, redissolved in THF, filtered, precipitated in petroleum ether, redissolved in THF and finally precipitated in methanol. The precipitate was collected and vacuum dried for nine hours at 60° C. The product was a powder having an average molecular weight by gel permeation chromatography comparison with polystyrene of $6.4 \times 10^3$.

B. Coupling of Trialkyl Amine

A solution of poly(chloromethylstyrene) (prepared in step A); (1.52 g, 10 mmole) in 50 ml of a one-to-one mixture of tetrahydrofuran and isopropanol was heated to reflux with stirring. Dimethyloctylamine (1.14 g, 7.25 mmole) was added and the reaction mixture was refluxed for 24 hours. This yielded the partially substituted poly(chloromethylstyrene) of the average formula

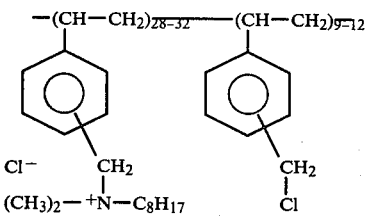

This product was not isolated. The entire reaction product was employed in step C.

C. Addition of Trialkanolamine

Triethanolamine (2.0 g, 13.4 mmole) was added to the reaction product of Part B, followed by 30 ml of isopropanol. The reaction mixture was then refluxed another 24 hours. At the conclusion of this reaction period, the homogenous mixture was cooled, diluted to three times its original volume with water, and the volatile constituents removed by in vacuo distillation (rotary evaporator). The residue, after concentration to one-half volume, was diluted with three volumes of 20% aqueous isopropanol and ultrafiltered through a 10,000 molecular-weight-cutoff cartridge (Amicon H1P10) with ten diavolumes of deionized water. The retentate was then concentrated by ultrafiltration to 100 ml and lyophilized to yield 2.46 g fluffy white solid of the formula

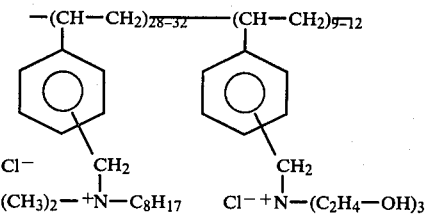

A solution of polychloromethylstyrene of Part A, Example I (1.52 g, 10 mmole) in 50 ml of one-to-one mixture of tetrahydrofuran and isopropanol was heated to reflux with stirring. Dimethyl hexylamine (1.42 g, 11 mmole) was added and the reaction mixture was refluxed 18 hours. After cooling, the homogeneous reaction mixture was diluted with water to three times its original volume, and the volatile constituents removed by distillation in vacuo (rotary evaporator). The residue after concentration by one-half was diluted with three volumes of water and ultrafiltered with deionized water (ten diavolumes) using a 10,000 molecular weight cutoff cartridge (Amico H1P10). Lyophilization afforded 2.6 g of fluffy white solid of the formula

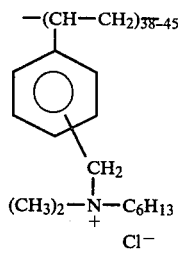

EXAMPLES III-VI and Comparative Experiments 1 and 2

The preparation of Example I was repeated substituting for dimethyloctylamine in equivalent amounts as follows:

| Comparative Experiment 1 | trimethylamine |
| Comparative Experiment 2 | dimethylethylamine |
| Example III | dimethyl-n-butylamine |
| Example IV | dimethyl-n-hexylamine |
| Example V | dimethyl-n-decylamine |
| Example VI | dimethyl-n-dodecylamine |
| Example VII | dimethyltetradecylamine |
| Example VIII | dimethylhexadecylamine |
| Comparative Experiment 3 | dimethyloctadecylamine |

Additional Illustrative Embodiments (A-O)

The preparations of Examples I and II are each repeated four times with the following changes:

A. In place of DP 38-45 poly(vinylbenzylchloride), a 38-45 DP poly(vinylbenzylbromide) prepared by polymerizing vinylbenzylbromide, is employed as precursor polymer.

B. In place of DP 38-45 poly(vinylbenzylchloride) an equal weight of DP 10-12 poly(vinylbenzylchloride) prepared by increasing the amount of initiator is employed as precursor polymer.

C. and D. In place of DP 38-45 poly(vinylbenzylchloride) equal weights of DP 100-125 and DP 300-350 poly(vinylbenzylchloride) are employed as precursor polymer.

E.-L. In place of DP 38-45 poly(vinylbenzylchloride) the following copolymers, prepared by free-radical copolymerizing the requisite monomers, are used in amounts to provide 10 mmole of available vinylbenzylchloride

| E. | 1:1 ratio | vinylbenzylchloride:styrene |
| F. | 1:1 ratio | vinylbenzylchloride:butadiene |
| G. | 1:0.5 ratio | vinylbenzylchloride:vinylacetamide |
| H. | 1:1 ratio | vinylbenzylchloride:acrylamide |
| I. | 1:0.5 ratio | vinylbenzyldimethyloctyl ammonium-chloride:4-vinylpyridine |
| J. | 1:1 ratio | vinylbenzyldimethyloctyl ammonium-chloride:4-vinylpyridine |
| K. | 1:0.5 ratio | vinylbenzyldimethyloctyl ammonium-chloride:N—vinylimidazole |
| L. | 1:0.5 ratio | vinylbenzylchloride:n-dodecyl-4-vinyl pyridinium chloride |

FORMULATION OF ANTIMICROBIAL PREPARATIONS

The quaternary ammonium group-containing products of the Examples and Illustrative Embodiments are formulated into antimicrobial preparations as follows:

Antimicrobial Solutions

A typical antimicrobial solution is prepared by dissolving 0.5% by weight of the product of Example I in sterile water, in a 25%/75% isopropanol/sterile water mixture, in a sterile saline solution adjusted to give isotonicity, and in an isotonic contact lens wetting solution containing 1% by weight poly(vinylalcohol).

An antimicrobial cleansing composition comprising 10% of the dry polymer of Example II and 90% powdered surfactant is prepared. When this composition is dissolved in water an antimicrobial solution results.

An antimicrobial salve is formulated by admixing 1% of the powder of Example I in a pharmaceutically acceptable poly saccharide gel.

Antimicrobial Testing

The materials of Examples I, II, III, IV, V, and VI were tested for antimicrobial activity. For purposes of comparison, Zephiran ® (a commerically accepted antimicrobial) and comparative materials 1, 2, and 3 were also evaluated.

Two basic test methods were used.

A. Broth dilution test. Dilutions of the test materials (10,25,50,100,250 ppm) or Zephiran ® (1,2,5,10,20 ppm) were prepared in 10 ml nutrient broth (BBL) (NB), or trypticase soy broth (TSB), inoculated with about $10^6$ CFU/ml Pseudomonas aeruginosa 15442, and incubated at 36° C. for seven days. MIC (Minimum Inhibition Concentration) is the lowest concentration resulting in no visible growth.

B. Effectiveness in saline. Test materials were added to sterile 0.9% NaCl to give 100 ppm solutions (0.01%). Zephiran ® was tested at 10 and 100 ppm. Tubes were innoculated with Pseudomonas aeruginosa 15442 at $2.7 \times 10^6$ CFU ml$^{-1}$ and incubated at 24° C. At 0.17, 0.5, 1, 2, 4, 6, 24, 48 and 72 hours after innoculation a loopful (1 mm loop) was removed and transferred to 10 ml trypticase soy broth, vortexed, and incubated at 35° for up to seven days. Cidal time is the time of the first sample showing no growth in the recovery media.

These two tests were repeated using other bacterial strains, as well.

With the material of Example I, the results shown in Table I were achieved. (For comparison, results with Zephiran ® are given as well.

TABLE I

| Test Organism | Test Material | Saline Test Conc. ppm | Saline Test Cidal Time (hr.) | Broth Test MIC, ppm NB | Broth Test MIC, ppm TSB |
|---|---|---|---|---|---|
| Pseudomonas aeruginosa 15442 | Example I | 0.2 | >48.00 | ≧50 | >100 |
| | | 0.5 | >48.00 | | |
| | | 1.0 | >48.00 | | |
| | | 2.0 | 2.00 | | |
| | | 5.0 | 0.50 | | |
| | | 10.0 | 0.50 | | |
| | | 25.0 | 0.17 | | |
| | | 50.0 | 0.17 | | |
| | | 50.0 + PG$^a$ | >48.00 | >100 + PG$^a$ | |
| | Zephiran ® | 10.0 | >48.00 | 10-20 | 50 |
| | | 25.0 | 1.00 | — | |
| | | 100.0 | <0.50 | | |
| | | 100.0 + PG$^a$ | <0.50 | ≦20 + PG$^a$ | |
| Staphylococcus aureus 6538 | Example I | 1.0 | >48.00 | 50 | >100 |
| | | 5.0 | 48.00 | | |
| | | 10.0 | 24.00 | | |
| | | 25.0 | 24.00 | | |
| | | 50.0 | 2.00 | | |
| | | 100.0 | <0.50 | | |
| | Zephiran ® | 10.0 | >48.00 | 1 | 1 |
| | | 25.0 | <0.50 | | |
| Escherichia coli 8739 | Example I | 1.0 | 2.00 | <10 | >10 |
| | | 5.0 | 1.00 | | |
| | | 10.0 | 0.17 | | |
| | | 25.0 | 0.17 | | |
| | | 50.0 | 0.17 | | |
| | Zephiran ® | 10.0 | 24.00 | <1 | 5 |
| | | 25.0 | 1.00 | | |
| Candida albicans 10231 | Example I | 10.0 | >48.00 | <50 | >50 |
| | | 25.0 | >48.00 | | |
| | | 50.0 | >48.00 | | |
| | | 100.0 | >48.00 | | |
| | Zephiran ® | 10.0 | >24$^L$ | <20 | <5 |
| | | 10.0 | 24$^S$ | | |
| | | 25.0 | 1.00 | | |

$^a$polygalacturonic acid, Na salt, 200 ppm.
$^L$Log phase cells
$^S$Stationary phase cells The Broth test with *Pseudomonas aeruginosa* was repeated using other materials:

| Test Material | Broth Dilution Test MIC, ppm | Cidal Time in Saline @100 ppm (hours) |
|---|---|---|
| Example III | >250 | >48 |
| Example IV | ≦50 | 0.17 |
| Example V | ≦100 | 0.6 |
| Example VI | ≦250 | 4 |
| Comparative 1 | >250 | >48 |
| Comparative 2 | >250 | >48 |
| Comparative 3 | ≧250 | 24 |

What is claimed is:

1. A compound having the structural formula:

$$-(CH-CH_2)_n-(CH-CH_2)_m-$$

with phenyl groups bearing $CH_2$ substituents:

$R-N^+-R'' \ X^- \quad X^- \ ^+N[(CH_2)_q-OH]_3$
$\quad |$
$\quad R'$ wherein R is a 4 to 12 carbon atom alkyl and R' and R'' independently are 1 to 4 carbon atom alkyls, X$^-$ is a physiologically acceptable anion, q is an integer from 2 to 4 and n and m are integers, the sum of which is from 20 to 10,000 with m being from 0.2 to 0.9 times the sum of m plus n.

2. The compound of claim 1 wherein R' and R'' are the same.
3. The compound of claim 1 wherein R is hexyl and R' and R'' are both methyls.
4. The compound of claim 1 wherein R is decyl and R' and R'' are both methyls.
5. The compound of claim 1 wherein R is dodecyl and R' and R'' are both methyls.
6. The compound of claim 1 wherein R is octyl.
7. The compound of claim 6 wherein R' and R'' are both methyls.
8. The compound of claim 7 wherein q is 2.
9. A compound having the structural formula:

$$-(CH-CH_2)_{\overline{28-32}}-(CH-CH_2)_{\overline{9-12}}-$$

with phenyl groups bearing $CH_2$ substituents:

$Cl^- \quad\quad\quad Cl^-$
$(CH_3)_2-^+N-C_8H_{17} \quad ^+N-(C_2H_4-OH)_3$

* * * * *